United States Patent
Salimi et al.

(10) Patent No.: US 10,426,490 B2
(45) Date of Patent: Oct. 1, 2019

(54) TRANSPARENT PRESSURE DRESSING DEVICE AND METHODS FOR ENABLING HEMOSTASIS OF BLOOD

(71) Applicants: Reza Salimi, Tehran (IR); Helia Salimi, Tehran (IR); Mohammad Arshia Salimi, Tehran (IR); Dorsa Salimi, Tehran (IR)

(72) Inventors: Reza Salimi, Tehran (IR); Helia Salimi, Tehran (IR); Mohammad Arshia Salimi, Tehran (IR); Dorsa Salimi, Tehran (IR)

( * ) Notice: Subject to any disclaimer, the term of this patent is extended or adjusted under 35 U.S.C. 154(b) by 291 days.

(21) Appl. No.: 15/485,176

(22) Filed: Apr. 11, 2017

(65) Prior Publication Data

US 2018/0014831 A1   Jan. 18, 2018

(30) Foreign Application Priority Data

Jul. 12, 2016 (IR) .................. 139550140003004674

(51) Int. Cl.
| | |
|---|---|
| *A61B 17/132* | (2006.01) |
| *A61B 17/08* | (2006.01) |
| *A61B 17/135* | (2006.01) |
| *A61B 17/00* | (2006.01) |
| *A61B 17/12* | (2006.01) |

(52) U.S. Cl.
CPC .......... *A61B 17/132* (2013.01); *A61B 17/085* (2013.01); *A61B 17/135* (2013.01); *A61B 17/1325* (2013.01); *A61B 2017/00557* (2013.01); *A61B 2017/00876* (2013.01); *A61B 2017/00907* (2013.01); *A61B 2017/00951* (2013.01); *A61B 2017/12004* (2013.01)

(58) Field of Classification Search
CPC .............. A61B 17/132; A61B 17/1322; A61B 17/1325; A61B 17/135; A61B 17/1355; A61B 17/12; A61B 2017/12004
See application file for complete search history.

(56) References Cited

U.S. PATENT DOCUMENTS

| | | | | |
|---|---|---|---|---|
| 5,263,965 | A * | 11/1993 | Roth ...................... | A61B 17/12 606/201 |
| 5,690,610 | A * | 11/1997 | Ito ....................... | A61F 13/0203 602/46 |
| 7,498,477 | B2 * | 3/2009 | Wada .................. | A61B 17/1325 602/53 |
| 2015/0305958 | A1 * | 10/2015 | Hoff ................... | A61B 17/1325 601/134 |

* cited by examiner

*Primary Examiner* — Sarah A Simpson

(57) ABSTRACT

A transparent pressure dressing device enables hemostasis of blood in a perforation of a blood vessel. The transparent pressure dressing device includes a rectangular plate shaped artificial hand component and one or more adhesive fins. The artificial hand component includes a protuberance section positioned proximal to a distal edge of the artificial hand component, and the adhesive fins extend from an upper surface of the artificial hand component. The protuberance section of the artificial hand component is gradually pressed against the perforation on the blood vessel to enable hemostasis of the blood, and the adhesive fins are configured to adhere to a body surface of a user proximal to the perforation on the blood vessel.

9 Claims, 9 Drawing Sheets

TRANSPARENT PRESSURE DRESSING DEVICE AND METHODS FOR ENABLING HEMOSTASIS OF BLOOD

BACKGROUND OF THE INVENTION

In the field of medical surgeries, many devices control and stop bleeding by putting pressure on the internal tissue of the body from the zone of the perforation in blood vessels. Several diagnostic and interventional procedures can be mentioned, such as coronary artery angiography and angioplasty, renal, carotid, organs, central venous angiography and angioplasty, etc. In these actions, there is a need for vascular access in many cases. The treatment is carried out with a diagnostic device by inserting cannula-like instruments, sometimes with a relatively large diameter. After the intravascular procedure, the cannula-like instruments must be taken out and the arterial puncture must be blocked to prevent bleeding.

Generally, coronary artery angiography is done through femoral artery in groin area by placing arterial sheath with different diameters. After angiography, arterial sheath must be removed from the artery; therefore, it is required to block the perforation in the blood vessel wall to stop the bleeding. Traditionally, a trained medical person puts pressure by hands on the tissue between the skin and the vessel wall at the zone of the puncture from the skin for approximately 20 minutes or more until the bleeding is stopped fully in the puncture created in the blood vessel. This process is difficult and exhausting for both health care workers and the patient. After the initial hemostasis, the zone of puncture is dressed, and then a three to five-kilogram sandbag is placed on the zone of the puncture for 6 hours. This method is still used in most medical centers. In this method, sanitation as well as infection and safety controls of both patients and health care workers using the sandbag are not sometimes observed appropriately and mistakes can happen. The major set of problems encountered in such a method is the use of multiple weights, pain in the lower back and groin area of the patient, difficulty with placement and the stability of the sandbag, mobility restrictions for the patient for a long time, and the lack of direct visibility of the hemostasis area.

Another method is using a metal device which consists of a metal plate placed under the groin of the patient and a vertical stand fixed at the end of the metal plate. The assembly is L-shaped and fixed, and placed on the vertical stand of another stand which is movable. The final component is a movable protuberance which transfers rotary press of the final component to the zone of the puncture. In this case, it is difficult to adjust the location of the compression zone and there is the possibility of relocation and partial obstruction of the arteries with the movement of the patient's femur and pelvis muscles. The pressure is reasonably high, intolerable and long for the patient.

Another method is using a balloon-like device at the zone of the puncture placed on the skin. The balloon-like device is fixed on the groin by long adhesive fins in the shape of a cross. Air or liquid is injected to the balloon bag through a pipe attached to the balloon which generates pressure at the blood vessel perforation. This device can be used after initial hemostasis. However, when the patient retracts his legs, the pressure which is put on the area is reduced and thus the possibility of bleeding and hematoma will be increased. Yet another method is using angio-seal device. In this method, the device stitches the arterial wall perforation which eventually leads to vessel hemostasis. However, in this method, there is the possibility of blood leakage from the stitches. Narrowing the blood vessel is also a probability with this method, and the blockage of a blood vessel or its lateral branches is possible.

Another method is using a Vaso-Seal device. In this method, a gelatinous substance is injected on the arterial wall perforation to create pressure by the support of surrounding tissues for hemostasis. But, in this method, there is the possibility of not creating an optimum pressure on the arterial perforation, and too much pressure may cause the probability of permeation of the gelatinous substance into the vein and the possibility of narrowing the blood vessel as well as thrombosis or occlusion. Thus, there are major problems during the usage of the prior art devices to enable hemostasis in skin puncture and femoral artery puncture. In venipuncture stages, artery perforation may be formed by angiographic needle at several points, the exact location of the blood vessel perforation may not be recognizable due to the angle of needle insertion into the skin and passing through different tissues between the skin and blood vessel in lean or obese patients.

Considering all the above-mentioned requirements, there is a need for a device which can create more comfort and less pain in the groin area or lower back of the patients, reduce vascular complications, create better mobility for patients, prevent the transmission of infection and providing more safety for the patient and healthcare workers, prevent trained medical staff fatigue as well as the waste of their time and energy. Further, there is a need for a device which can provide better control in treatment stages of the patients, and to avoid pressure fluctuations in the zone of femoral artery hemostasis because pressure fluctuations in the zone of the puncture can cause subcutaneous hemorrhage or hematoma in the zone of the puncture. In addition, in the case of the infection of sandbags made of fabric or artificial leather, the risk of the transmission of nosocomial infections to other patients or healthcare workers can be increased since it's impossible to clean. When the sand and soil pour out from the sandbag steadily, the contamination of angiography room will be also possible. So, the anticipated device should avoid such contaminations and infections which could be caused by use of conventional exiting devices and methods.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

A transparent pressure dressing device enables hemostasis of blood in a perforation of a blood vessel. The transparent pressure dressing device comprises a rectangular plate shaped artificial hand component and one or more adhesive fins. The artificial hand component comprises a protuberance section positioned proximal to a distal edge of the artificial hand component, and the adhesive fins extend from an upper surface of the artificial hand component. The protuberance section of the artificial hand component is gradually pressed against the perforation on the blood vessel to enable hemostasis of the blood, and the adhesive fins are configured to adhere to a body surface of a user proximal to the perforation on the blood vessel.

In an embodiment, transparent pressure dressing device further comprises one or more metal weight components positioned above and conforming to the upper surface of the artificial hand component. Each metal weight component is configured to add weight to the artificial hand component to increase the pressure applied to enable hemostasis of the blood at the perforation of the blood vessel. In an embodiment, transparent pressure dressing device further comprises multiple magnetic pieces positioned on an upper surface of the metal weight component. The magnetic pieces allow attachment of one or more metal weight components above the artificial hand component to generate required compression on body's tissues proximal to the perforation of the blood vessel.

In an embodiment, the surface of the magnetic pieces is one of electroplated and stretched with a cover made of polymer material to preserve an integral surface of attachment. In an embodiment, transparent pressure dressing device further comprises a transparent adhesive plastic layer positioned on the surface of the artificial hand component, and the adhesive plastic layer enables alignment of the magnetic pieces and the adhesive fins. In an embodiment, the protuberance section transfers pressure to underlying tissues proximal to the perforation of the blood vessel to block the blood flow at the perforation, thereby stopping the bleeding through hemostasis. In an embodiment, transparent pressure dressing device further comprises a trapezoid shaped shoe member. The shoe member is configured to conform to the surface of the protuberance section, and the shoe member adds height to the protuberance section to enable a deeper application of pressure at the perforation on the blood vessel.

In an embodiment, transparent pressure dressing device further comprises a balloon member removably attached above the artificial hand component, and a vented pipe is attached to the balloon member to define a fluid communication with the balloon member. A fluid is pumped into through the vented pipe to expand the balloon member to increase pressing pressure at the perforation on the blood vessel via the artificial hand component. In an embodiment, the artificial hand component is disposable after the hemostasis of the blood is completed. In an embodiment, the metal weight components are re-usable after the hemostasis of the blood is completed, and the metal weight components are re-usable via cleaning and disinfection. In an embodiment, another set of adhesive fins are attached to bottom corners of the artificial hand component to adhere to the body surface of the patient proximal to the perforation on the blood vessel.

A method of enabling hemostasis of blood in a perforation of a blood vessel is disclosed herein. A transparent pressure dressing device is provided and comprises a rectangular plate shaped artificial hand component and one or more adhesive fins, as discussed above. The method steps involve; marking the perforation of the blood vessel using a marker, aligning the protuberance section of the artificial hand component against the marked perforation on the blood vessel, removing a cover of adhesive fins positioned on the upper surface of the artificial hand component, controlling the bleeding at the perforation by gradually applying pressure using the hand of trained personnel on the artificial hand component, wherein the protuberance section is pressed against the perforation of the blood vessel, positioning one or more metal weight components above the artificial hand component, attaching the adhesive fins proximal to the perforation of the blood vessel, and retaining the transparent pressure dressing device over the perforation of the blood vessel for a predefined time until the hemostasis of blood is observed in the perforation of the blood vessel.

In an embodiment, a first set of the adhesive fins are attached to a leg of the patient, and one of the adhesive fins is attached on the abdomen toward an upper edge of a pelvis bone of a front leg, and the other adhesive fin on a side of the patient and upper edge of the pelvis bone of the leg. In an embodiment, a second set of the adhesive fins are removed and attached to the skin of the lower section of the patient's groin, on both internal and external sides of the patient's groin.

One aspect of the present disclosure is a transparent pressure dressing device configured to enable hemostasis of blood in a perforation of a blood vessel. The device comprises: a) a rectangular plate shaped artificial hand component, wherein the artificial hand component comprises a protuberance section positioned proximal to a distal edge of the artificial hand component; and b) one or more adhesive fins extending from an upper surface of the artificial hand component, wherein the protuberance section of the artificial hand component is gradually pressed against the perforation on the blood vessel to enable hemostasis of the blood, and the adhesive fins are configured to adhere to a body surface of a patient proximal to the perforation on the blood vessel.

In one embodiment, the transparent pressure dressing further comprises one or more metal weight components positioned above and conforming to the upper surface of the artificial hand component, wherein each metal weight component is configured to add weight to the artificial hand component to increase the pressure applied to enable hemostasis of the blood at the perforation of the blood vessel. In another embodiment, the transparent pressure dressing device further comprises a plurality of magnetic pieces positioned on an upper surface of the metal weight component, wherein the magnetic pieces allows attachment of one or more metal weight components above the artificial hand component to generate required compression on body's tissues proximal to the perforation of the blood vessel. In one embodiment, the surface of the magnetic pieces is one of electroplated and stretched with a cover made of polymer material to preserve an integral surface of attachment. In another embodiment, the transparent pressure dressing device further comprises a transparent adhesive plastic layer positioned on the surface of the artificial hand component, wherein the adhesive plastic layer enables alignment of the magnetic pieces and the adhesive fins.

In one embodiment, the protuberance section transfers pressure to underlying tissues proximal to the perforation of the blood vessel to block the blood flow at the perforation, thereby stopping the bleeding through hemostasis. In another embodiment, the transparent pressure dressing device further comprises a trapezoid shaped shoe member, wherein the shoe member is configured to conform to the surface of the protuberance section, wherein the shoe member is configured to provide added height to the protuberance section to enable a deeper application of pressure at the perforation on the blood vessel. In one embodiment, the transparent pressure dressing device further comprises a balloon member removably attached above the artificial hand component, wherein a vented pipe is attached to the balloon member to define a fluid communication with the balloon member, wherein a fluid is pumped into through the vented pipe to expand the balloon member to increase pressing pressure at the perforation on the blood vessel via the artificial hand component.

In one embodiment of the transparent pressure dressing device, the artificial hand component is disposable after the hemostasis of the blood is completed. In another embodiment, the metal weight components are re-usable after the hemostasis of the blood is completed, wherein the metal weight components are re-usable via cleaning and disinfection. In yet another embodiment of the transparent pressure dressing device, another set of adhesive fins are attached to bottom corners of the artificial hand component to adhere to the body surface of the patient proximal to the perforation on the blood vessel.

Another aspect of the present disclosure is directed to a method of enabling hemostasis of blood in a perforation of a blood vessel. The method comprises: (a) providing a transparent pressure dressing device comprising (i) a rectangular plate shaped artificial hand component, wherein the artificial hand component comprises a protuberance section positioned proximal to a distal edge of the artificial hand component; and (ii) one or more adhesive fins extending from an upper surface of the artificial hand component; (b) marking the perforation of the blood vessel using a marker; (c) aligning the protuberance section of the artificial hand component against the marked perforation on the blood vessel; (d) removing a cover of adhesive fins positioned on the upper surface of the artificial hand component; (e) controlling the bleeding at the perforation by gradually applying pressure using the hand of trained personnel on the artificial hand component, wherein the protuberance section is pressed against the perforation of the blood vessel; (f) positioning one or more metal weight components above the artificial hand component; (g) attaching the adhesive fins proximal to the perforation of the blood vessel; and (h) retaining the transparent pressure dressing device over the perforation of the blood vessel for a predefined time until the hemostasis of blood is observed in the perforation of the blood vessel.

In one embodiment, a first set of the adhesive fins are attached to a leg of the patient, wherein one of the adhesive fins is attached on the abdomen toward an upper edge of a pelvis bone of a front leg, and the other adhesive fin on a side of the patient and upper edge of the pelvis bone of the leg. In another embodiment, a second set of the adhesive fins are removed and attached to the skin of the lower section of the patient's groin, on both internal and external sides of the patient's groin.

In one embodiment, a shoe member with a suitable height is positioned over the protuberance section to increase the height of the raised protuberance section of the artificial hand component, wherein the shoe member enables to contact a blood vessel which is deeply positioned under the skin of the patient. In another embodiment, the method further comprises removably attaching a balloon member above the artificial hand component, wherein a vented pipe is attached to the balloon member to define a fluid communication with the balloon member. In a related embodiment, a fluid is pumped into through the vented pipe to expand the balloon member to increase pressing pressure at the perforation on the blood vessel with the artificial hand component.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and components disclosed herein.

DETAILED DESCRIPTION

The present invention generally relates to a device used to stop blood flow or enable hemostasis of blood in the field of medical surgery, and more particularly relates to a transparent pressure dressing device configured to enable hemostasis of blood in a perforation of a blood vessel.

Figure 1:
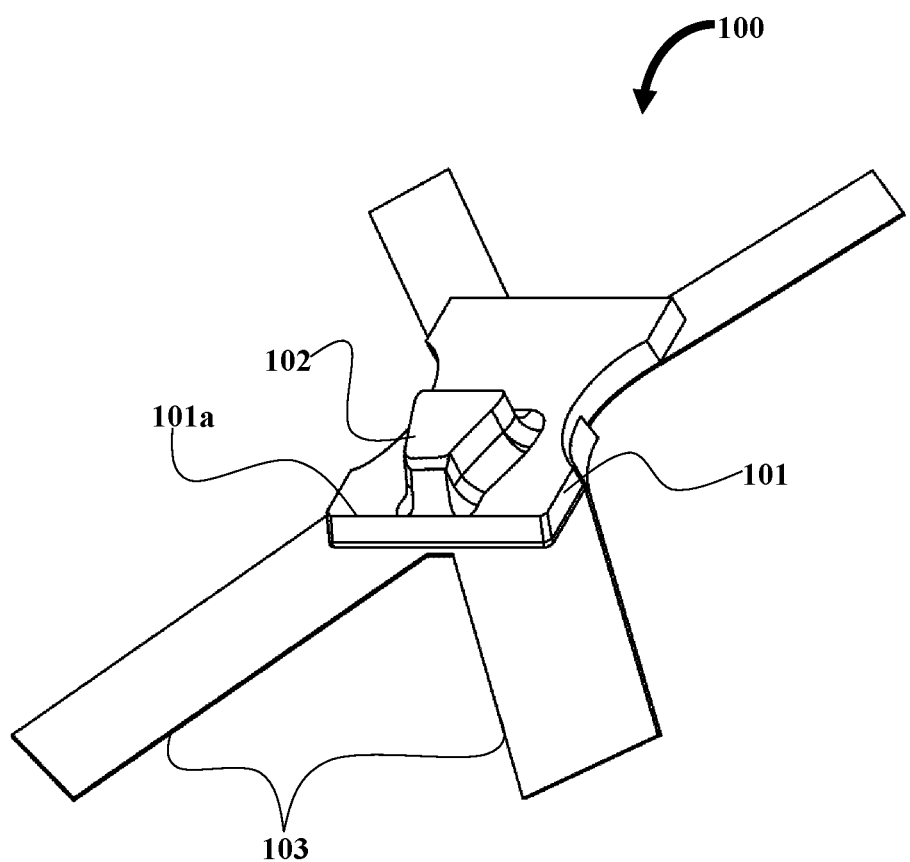
FIG. 1 exemplarily illustrates a front perspective view of the transparent pressure dressing device.

FIG. 1 exemplarily illustrates a front perspective view of the transparent pressure dressing device 100. The transparent pressure dressing device 100 configured to enable hemostasis of blood in a perforation 602 of a blood vessel. The transparent pressure dressing device 100 comprises a rectangular plate shaped artificial hand component 101 and one or more adhesive fins 103. The artificial hand component 101 comprises a protuberance section 102 positioned proximal to a distal edge 101a of the artificial hand component 101, and the adhesive fins 103 extend from an upper surface of the artificial hand component 101. The protuberance section 102 of the artificial hand component 101 is gradually pressed against the perforation 602 on the blood vessel to enable hemostasis of the blood, and the adhesive fins 103 are configured to adhered to a body surface of a user proximal to the perforation 602 on the blood vessel. The blood vessel is hereinafter referred to as, for example, an artery or a vein, especially a femoral artery with respect to the following description.

Figure 2A:
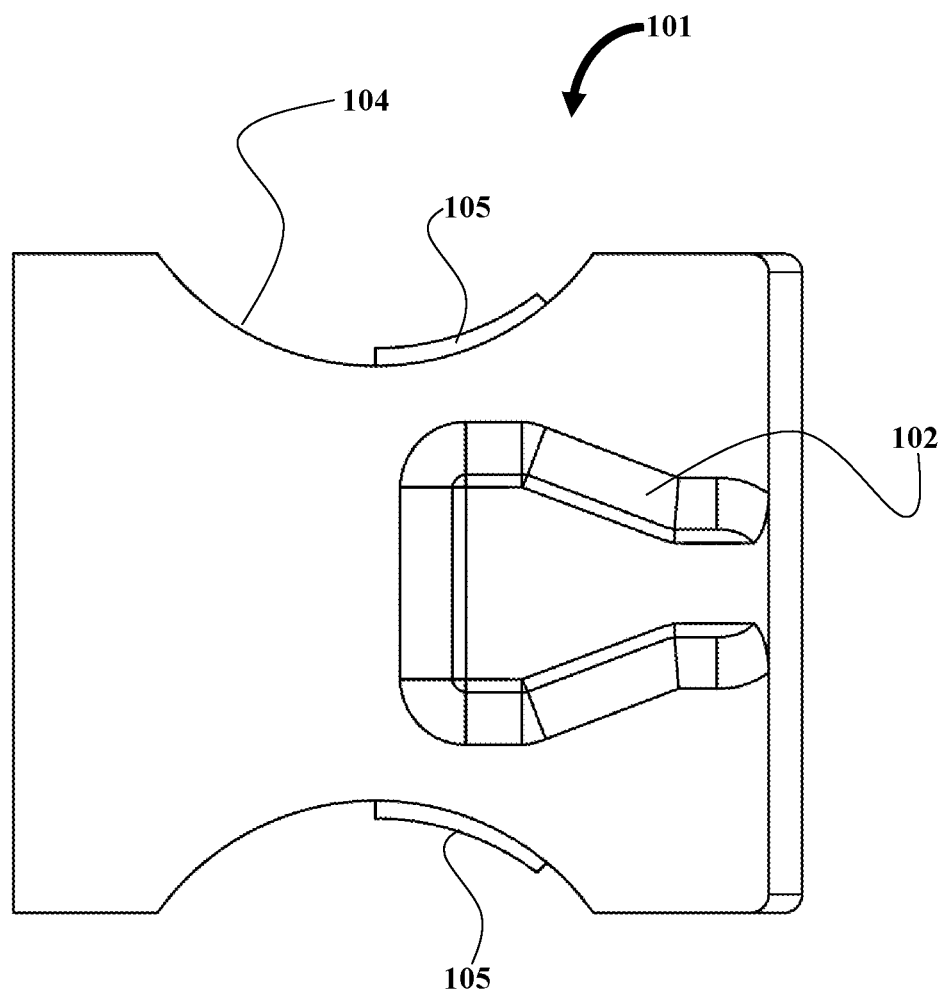
FIG. 2A exemplarily illustrates a top plan view of the artificial hand component.
Figure 2B:
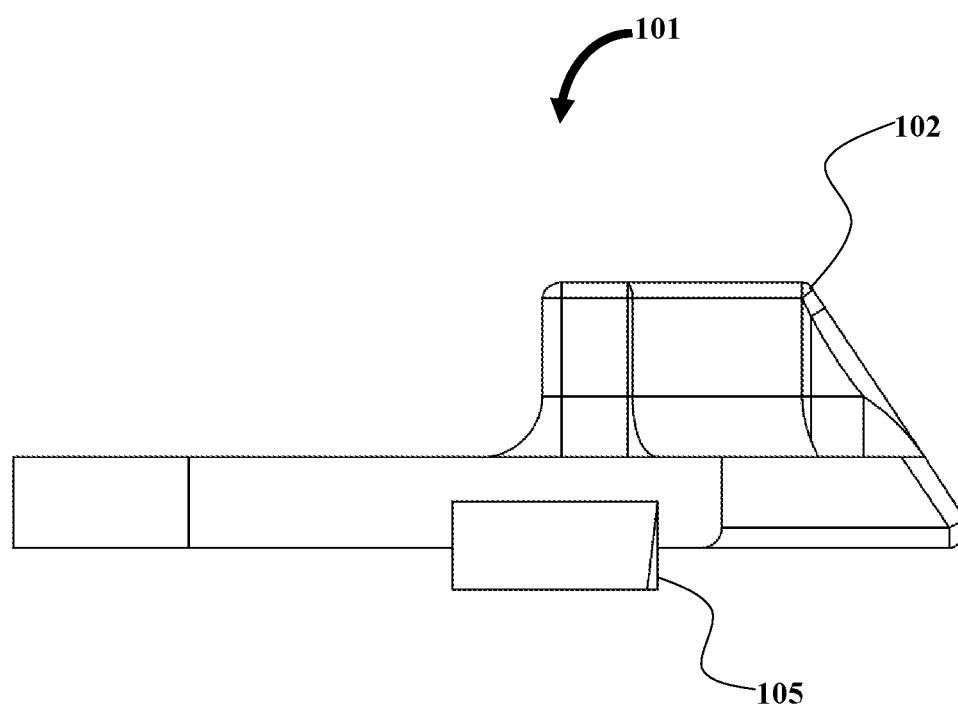
FIG. 2B exemplarily illustrates a side view of the artificial hand component.

FIGS. 2A-2B exemplarily illustrates a top plan view and a side view of the artificial hand component 101. The artificial hand component 101 is rectangular in shape with a length of, for example, 110 millimeter (mm) and width of 90 mm. There is a curve-like depression 104 from the side of the rectangle's lengths. From a transverse middle section to the inside from the top portion, there is a distance of 5 mm, and from the bottom with 15 mm to the inner surface of the artificial hand component 101. There are two-iron pieces 105 with, for example, the thicknesses of 2 mm and a dimension of 10×10 mm which are installed and fixed in a place. From the above, in the depressions 104 of the artificial hand component 101 in longitudinal side, there is a protuberance with the thickness of, for example, 2 mm and the height of 5 mm which is the site of the operator's hand to be placed and a supporter for a metal weight component 106, as discussed further in the detailed description.

On the upper surface of the artificial hand component 101, in the corners, from the edge of the corner at the top, the adhesive fin 103 or a hypoallergenic adhesive tape with the length of, for example, 120 mm and the width of 50 mm, is placed in the shape of a cross which is in contact with the patient's skin. In the bottom corners, another set of adhesive fin 103 or hypoallergenic adhesive tape, for example, with the length of 80 mm and the width of 30 mm, is placed in the shape of a cross which is in contact with the patient's skin. In an embodiment, a transparent adhesive plastic layer is placed on the surface of the artificial hand component 101 which does not prevent the visibility of the underlying sections is stretched on the artificial hand component 101 to equalize coverage and help in fixing or aligning the iron pieces and hypoallergenic adhesive fins 103.

The cross-sectional portion as seen from the middle section of the artificial hand component 101 includes a surface, for example, with a thickness or depth of 10 mm-30 mm and length of 110 mm in a distance between 20-50 mm at the top of the patient's head along with the artificial hand component 101, as well as two depressions with the length of 10 mm and depth of 2 mm in the line above the artificial hand component 101 which is a site for placing iron pieces. In the most raised surface, at the cross-sectional part of the artificial hand component 101, as seen from the beneath, there is a trapezoid-like protuberance section 102 which positioned at the site of creating effective pressure to control bleeding. The protuberance section 102 has a length of 30 mm, and a width of 30 mm at maximum and 15 mm at minimum, and the protuberance section 102 transfers pressure to underlying tissues to block the zone of artery perforation 602 and stops bleeding. The location of the point conforming to the point of needle insertion and the zone of skin perforation 602 is in a shape of a circular mark with a diameter of 2 mm which is marked by a selected color.

Due to the length and width of the contact surface, the main location of the application of pressure using the protuberance section 102 is, for example, length 30 mm and width 30 mm at maximum, and 15 mm at minimum. Adequate pressure for producing effective pressure on the zone of artery perforation 602 will be anticipated according to the angle of middle insertion and the depth of the artery from the skin surface of the user. The artificial hand component 101 is placed on the intended area, then colored marker is placed on the insertion site of the arterial sheath into the skin, in a way that the small base of the trapezoid protuberance section 102 is placed along the femoral artery. Now, a moderate pressure is applied by trained healthcare workers, and the arterial sheath will be taken out to the extent that the bleeding is controlled. Next, the adhesive fins 103 are attached and the metal weight component 106, with the required amount of weight, is placed on the artificial hand component 101 so that the bleeding is fully stopped, at the same time allowing to continue the blood flow in the distal arteries.

One aspect of the present disclosure is a transparent pressure dressing device configured to enable hemostasis of blood in a perforation of a blood vessel. The device comprises a rectangular plate shaped artificial hand component, wherein the artificial hand component comprises a protuberance section positioned proximal to a distal edge of the artificial hand component. The device further comprises one or more adhesive fins extending from an upper surface of the artificial hand component, wherein the protuberance section of the artificial hand component is gradually pressed against the perforation on the blood vessel to enable hemostasis of the blood, and the adhesive fins are configured to adhere to a body surface of a patient proximal to the perforation on the blood vessel.

The transparent pressure dressing may further comprise one or more metal weight components positioned above and conforming to the upper surface of the artificial hand component. Each metal weight component may be configured to add weight to the artificial hand component to increase the pressure applied to enable hemostasis of the blood at the perforation of the blood vessel. The transparent pressure dressing device may further comprise a plurality of magnetic pieces positioned on an upper surface of the metal weight component, wherein the magnetic pieces allows attachment of one or more metal weight components above the artificial hand component to generate required compression on body's tissues proximal to the perforation of the blood vessel. The surface of the magnetic pieces may be one of electroplated and stretched with a cover made of polymer material to preserve an integral surface of attachment. The transparent pressure dressing device may further comprise a transparent adhesive plastic layer positioned on the surface of the artificial hand component, wherein the adhesive plastic layer enables alignment of the magnetic pieces and the adhesive fins.

Figure 3:
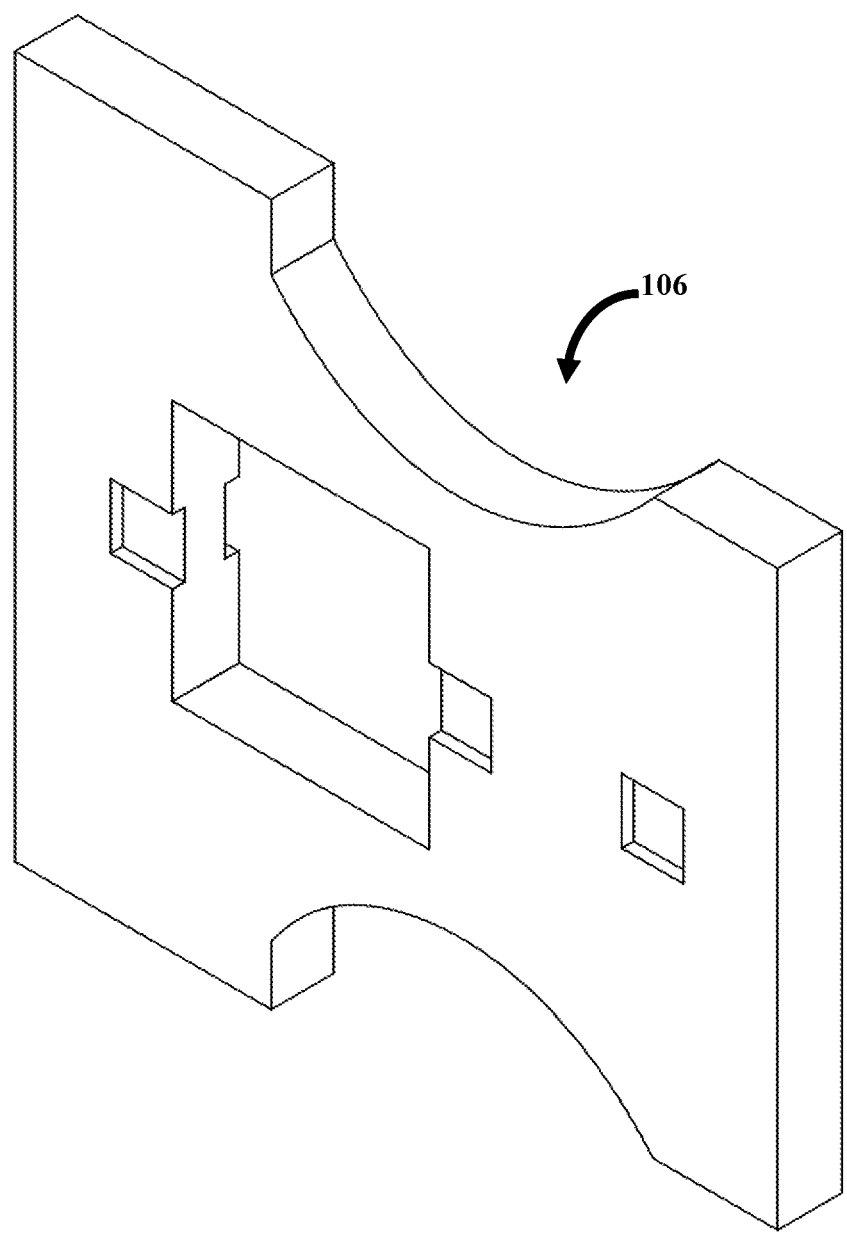
FIG. 3 exemplarily illustrates a side perspective view of the metal weight component.

FIG. 3 exemplarily illustrates a side perspective view of the metal weight component 106. In an embodiment, the transparent pressure dressing device 100 further comprises one or more metal weight components 106 positioned above and conforming to an upper surface of the artificial hand component 101, wherein each metal weight component 106 is configured to add weight to the artificial hand component 101 to increase the pressure applied to enable hemostasis of blood at the perforation 602 of the blood vessel. The metal weight component 106 adds weight pressure on the artificial hand component 101 and transfers the pressure to the zone of the vessel perforation 602, and enables the compression of the tissues on the blood vessels.

The length and width of the metal weight component 106 is, for example, 120 mm and 90 mm respectively. The metal weight component 106 conforms to the artificial hand component 101. From a top part of the edge of the arc of the lateral depression, on both sides, 10 mm is added to the width of the metal weight component 106. From the top part of the artificial hand component 101, the enhancement of the length is performed. The width of the upper side of the metal weight component 106 is designed to 110 mm. The thickness of the metal weight component 106 is selected based on the weight requirement. From the above side of the metal weight component 106 and from the beginning of the partition of the upper edge, there is a vacant space between 25 mm-65 mm conformed to the transparent part of the artificial hand component 101.

The metal weight component 106 is made of, for example, metals or heavy materials with high density such as lead, copper, zinc, ceramics, brass alloy, etc. On the lower surface of the metal weight component 106, there are three pieces with magnetism with the length of, for example, 10 mm and width of 10 mm and thickness of 2 mm; from the center line of the metal piece, or from the patient's head. The first magnetic piece detaches 15 mm from the upper edge toward the bottom of the metal piece. The second piece is placed in the same direction with a distance of, for example, 55 mm; the third piece is installed from the terminal edge of the metal piece in the same direction with a distance of 15 mm.

In another embodiment, multiple magnetic pieces are positioned on an upper surface of the metal weight component 106, wherein the magnetic pieces allow attachment of one or more metal weight components 106 above the artificial hand component 101 to generate required compression on the body's tissues proximal to the perforation 602 of the blood vessel. The magnetic pieces are placed on the upper surface of the metal weight component 106, similar to how it is placed in the lower surface. In the depression surface with the dimensions of, for example, 10×10 mm and depth of 2 mm, iron or magnetic plates in the shape of square, circle, etc. are installed so that in the case of requirement of additional weight, it is possible to add weights on each other, and therefore provide the required weight to produce appropriate compression on the body's tissues. Based on the needs, the weights of the metal weight component 106 are changeable to different weight with the same shape but just by increasing or decreasing the thickness. The entire surface of the magnetic pieces is electroplated or stretched with a cover made of polymer material or other appropriate material to preserve an integral surface of attachment. In this case, the possibility of proper cleaning as well as the conditions for infection control will be provided.

The protuberance section may transfer pressure to underlying tissues proximal to the perforation of the blood vessel to block the blood flow at the perforation, thereby stopping the bleeding through hemostasis. The transparent pressure dressing device may further comprise a trapezoid shaped shoe member, wherein the shoe member is configured to conform to the surface of the protuberance section, wherein the shoe member is configured to provide added height to the protuberance section to enable a deeper application of pressure at the perforation on the blood vessel. The transparent pressure dressing device may further comprise a balloon member removably attached above the artificial hand component, wherein a vented pipe is attached to the balloon member to define a fluid communication with the balloon member, wherein a fluid is pumped into through the vented pipe to expand the balloon member to increase pressing pressure at the perforation on the blood vessel via the artificial hand component.

The artificial hand component may be disposable after the hemostasis of the blood is completed. Yet, the metal weight components are re-usable after the hemostasis of the blood is completed, wherein the metal weight components are re-usable via cleaning and disinfection. In one example of the transparent pressure dressing device, another set of adhesive fins are attached to bottom corners of the artificial hand component to adhere to the body surface of the patient proximal to the perforation on the blood vessel.

Figure 4A:
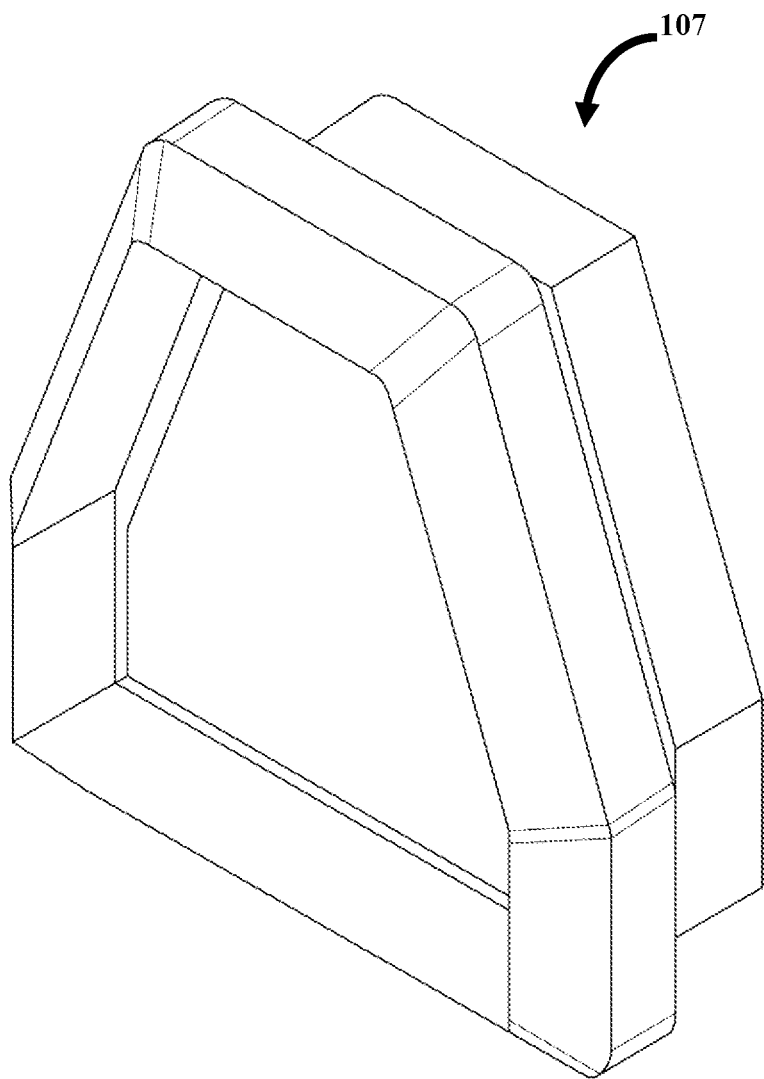
FIG. 4A exemplarily illustrates a side perspective view of the shoe member.
Figure 4B:
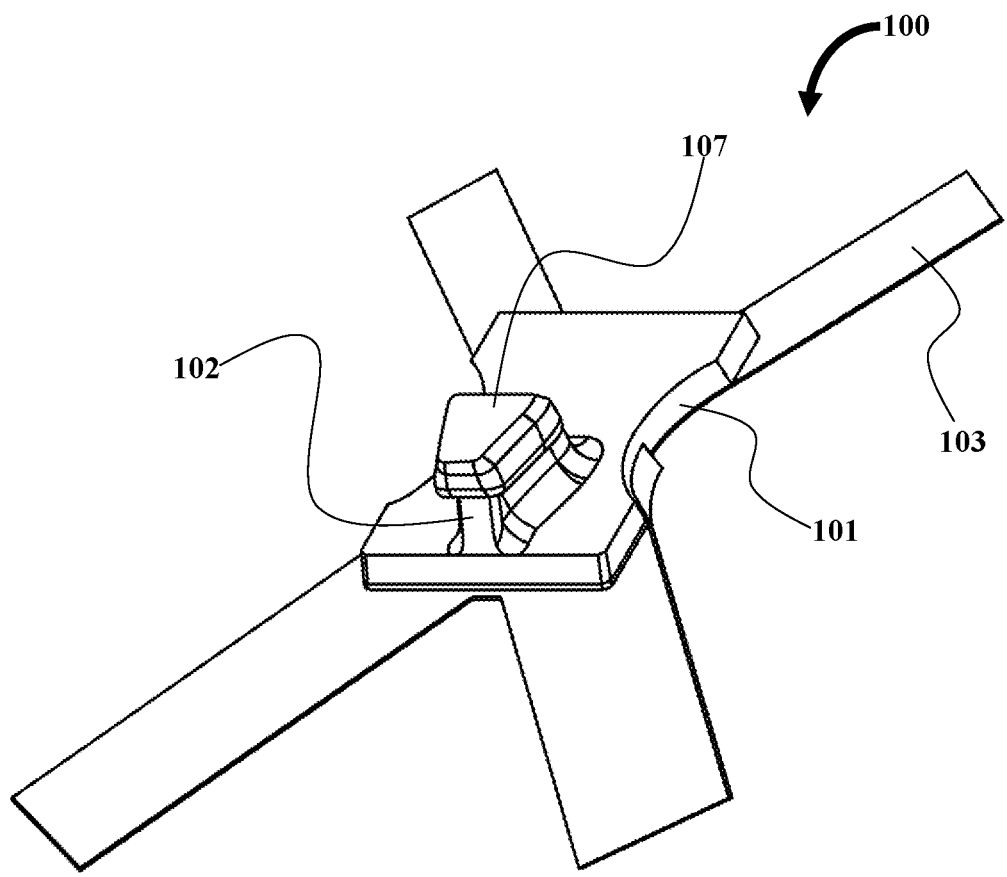
FIG. 4B exemplarily illustrates a top perspective view of the shoe member attached to the protuberance section of the artificial hand component.

FIG. 4A exemplarily illustrates a side perspective view of the shoe member 107, and FIG. 4B exemplarily illustrates a top perspective view of the shoe member 107 attached to the protuberance section 102 of the artificial hand component 101. In an embodiment of the transparent pressure dressing device 100, a shoe member 107 is configured to conform to the surface of the protuberance section 102, and the shoe member 107 is configured to provide added height to the protuberance section 102 to enable a deeper application of pressure at the perforation 602 on the blood vessel.

A transparent pressure dressing defines the process through which the transparent pressure dressing device 100 is fixed on the perforation 602 on the blood vessel, for example, the femoral artery. The transparent pressure dressing device 100 is used to block the zone of femoral artery perforation 602 after taking actions such as coronary angiography to stop bleeding and hematoma caused by the created perforation 602 in the artery. The following two models can be used to increase the height.

In a first method or embodiment, where there is a requirement for more height in the trapezoid-shaped protuberance section 102 in lean or obese patients, a component called "shoe" is used. By attaching the shoe member 107 to the required height, the artificial hand component 101 will be ready to use. The shoe member 107 is fully conformed to the trapezoid-shaped protuberance section 102 and attached and fixed on it. With the use of the shoe member 107, it is possible to increase the height of trapezoid protuberance section 102, and required thickness for transferring effective pressure will be provided in lean and obese patients. The shoe member 107 obviates the need for diversifying the [different] types of transparent pieces.

Figure 5A:
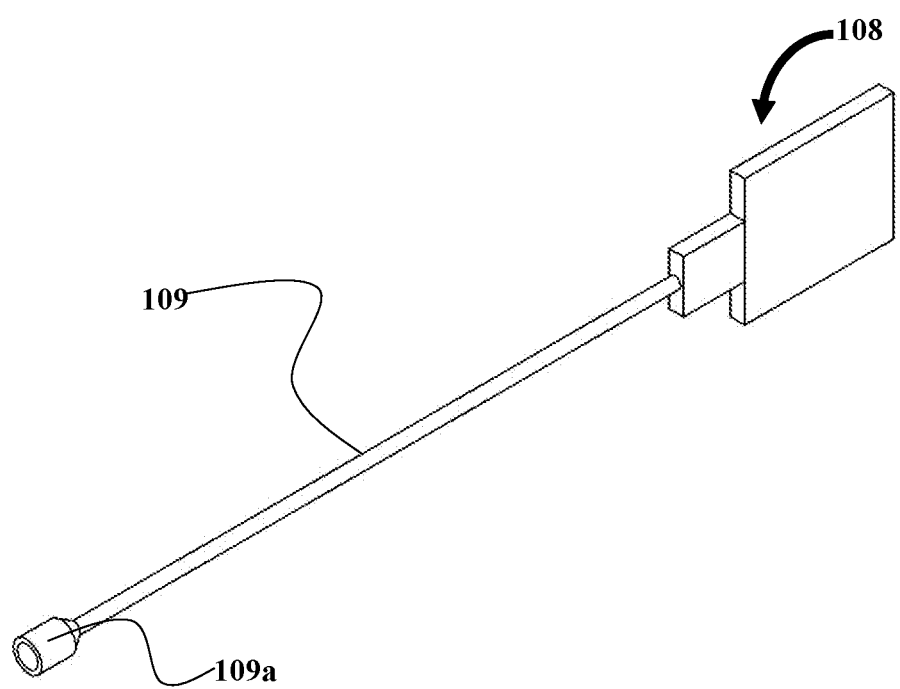
FIG. 5A exemplarily illustrates a top perspective view of the balloon member.
Figure 5B:
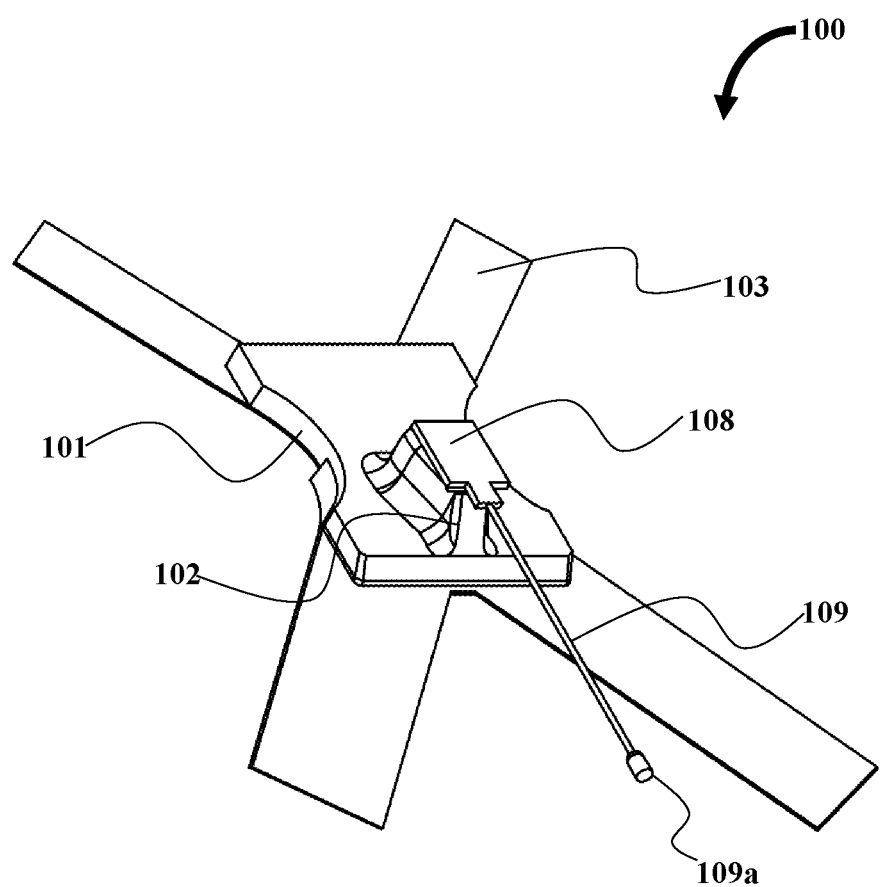
FIG. 5B exemplarily illustrates a top perspective view of the balloon member attached to the protuberance section of the artificial hand component.

FIG. 5A exemplarily illustrates a top perspective view of the balloon member. FIG. 5B exemplarily illustrates a top perspective view of the balloon member attached to the protuberance section of the artificial hand component. In an embodiment of the transparent pressure dressing device 100, a balloon member 108 is removably attached above the artificial hand component 101. A vented pipe 109 is attached to the balloon member 108 to define a fluid communication with the balloon member 108, and a fluid is pumped into through the vented pipe 109 to expand the balloon member 108 to increase pressing pressure at the perforation 602 on the blood vessel via the artificial hand component 101.

As discussed previously about the transparent pressure dressing, a second method of transparent pressure dressing involves the balloon member 108, for example, with a length of 40 mm and width of 10 to 35 mm to which a vented pipe 109 with the length of 120 mm is attached, and a vent 109a is attached at the distal end of the vented pipe 109. This balloon member 108 is attached to the bottom of the trapezoid-shaped protuberance section 102 of the artificial hand component 101. The height of the protuberance section 102 of the artificial hand component 101 will be increased to the extent necessary after injecting air via a syringe into the balloon member 108. This controls bleeding and reducing the possible stiffness or rigidity of the terminal trapezoid-shaped protuberance section 102 of the artificial hand component 101.

For example, in obese patients and in cases where there is blood leakage from the zone of the perforation 602, it will be possible to increase the height of the transparent protuberance section 102 from a few millimeters to a few centimeters by blowing up the balloon member 108, at the end of the transparent protuberance section 102, under the trapezoid-shaped surface. Therefore, the pressure will be concentrated on the given zone and cause better transference of the force produced by weight on the zone.

Then, in order to maintain pressure and not to waste time and energy of healthcare workers, instead of the pressure produced by the hands of the trained personnel, metal weights defined by the metal weight component 106 are placed on the artificial hand component 101 to the extent necessary pressure. The weights and the artificial hand component 101 are fixed together. The zone of the skin perforation 602 and the location of the arterial sheath insertion are seen and controlled by the trained personnel. The number of weights is set on the artificial hand component 101 with respect to amount of control of the bleeding required according to the pulse control of the foot, and the zone of skin perforation 602.

By looking at the zone of the skin perforation 602 from two sides of the artificial hand component 101 which has a 15-mm depression, as well as seeing the transparent area of the artificial hand component 101 from the above which is without any coverage, it is possible for the trained personnel to see the zone of the skin perforation 602 from the above and sides, thereby enabling them to control the bleeding as well as the probable hematoma.

To summarize, the main components of the transparent pressure dressing device 100 comprises the artificial hand component 101, the metal weight component 106, the magnetic components, and the shoe member 107 or balloon member 108. The artificial hand component 101 is made of transparent materials, and comprises the protuberance section 102 with trapezoid-shaped surface, with a length of 30 mm and a width of 15-30 mm placed over the skin on the zone of the perforation 602 along with the vein. In the upper surface, magnetic components are installed and the artificial hand component 101 with the adhesive tapes fixed at the location in the shape of a cross. Now, small weights with high density along with small pieces of magnets are placed on the artificial hand component 101, and due the magnetic force, the connection will be established.

In lean and obese patients, the shoe member 107 or the balloon member 108 is installed on a trapezoid-shaped protuberance section 102 for increasing the required height, and are used in order to transfer appropriate weight pressure to underlying tissues of the body and to block the zone of artery perforation 602. All applied components have been designed in a way that the zone of artery perforation 602 to be visible. The application of the transparent pressure dressing device 100 is very simple from the moment of the removal of the arterial sheath to the end of the hemostasis process effective on the patient and medical personnel.

Figure 6:
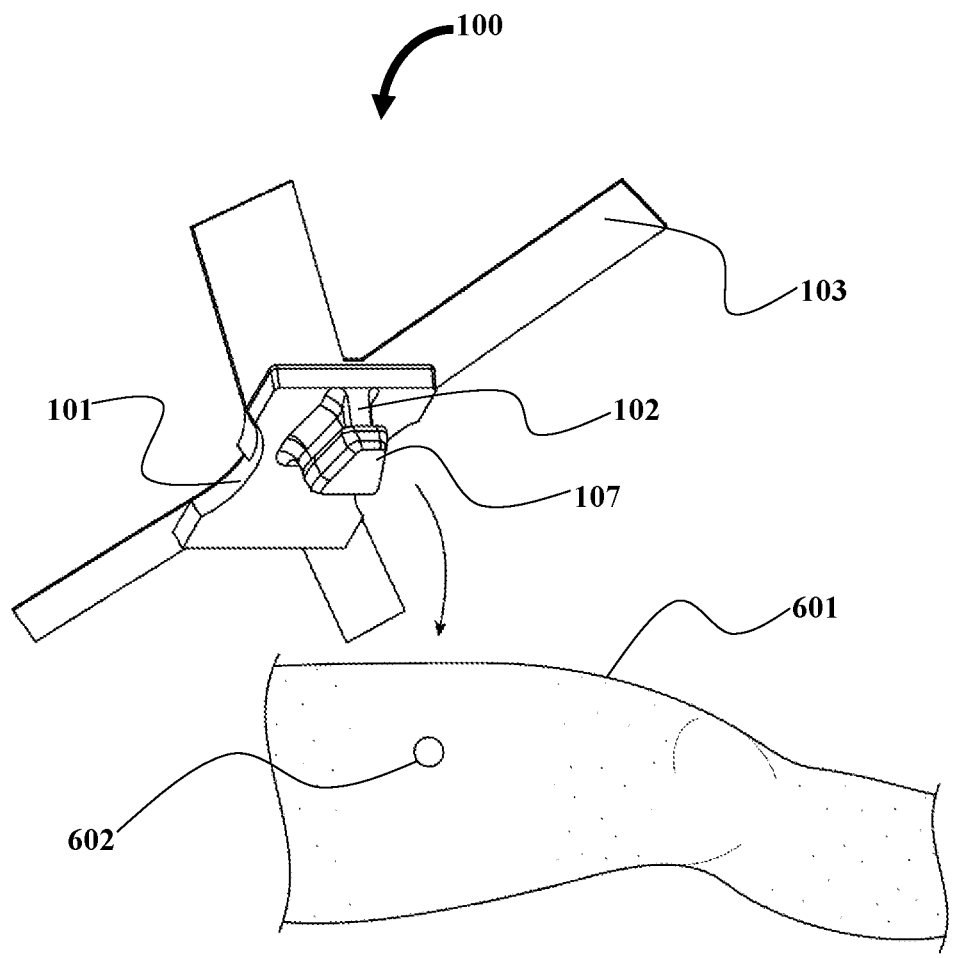
FIG. 6 exemplarily illustrates a method of application of the transparent pressure dressing device at the perforation on the blood vessel.

FIG. 6 exemplarily illustrates a method of application of the transparent pressure dressing device 100 at the perforation 602 on the blood vessel. Considering the method for the application of the transparent pressure dressing device 100, the method is applied after finishing coronary angioplasty through the femoral artery on the leg 601 of a user, and this transparent pressure dressing device 100 can be used to block the zone of the perforation 602 and control bleeding after arterial sheath removal. The method of application is explained below; Initially, the perforation 602 is marked with a circular marker, and the trapezoid protuberance section 102 is aligned with the mark made by the circular marker on the surface of the skin, the artificial hand component 101 is placed on the zone of the skin perforation 602, or the site of arterial sheath insertion in a way that the small side of the trapezoid protuberance is placed on the path of passing the artery toward the head of the patient.

Then, the cover of the upper adhesive fins 103, installed on the artificial hand component 101, is removed. Next, the adhesive fins 103 are attached, one of them on the abdomen toward the upper edge of the pelvis bone of the front leg, and the other, on the side of the patient and upper edge of the pelvis bone of the leg under hemostasis. After attaching the upper adhesive fins 103, the arterial sheath is removed and the bleeding of the zone of the perforation 602 is controlled by applying pressure using the hand of a trained personnel on the upper surface of the artificial hand component 101. Then, by observing the area and final set, the cover of the lower adhesive fins 103 is removed and the adhesive fins 103 are attached to the skin, on both internal and external sides of the patient's groin.

When the artery of the patient is deeper, as in the case of obese patients, and the required pressure is not transferred properly to the zone of the perforation 602 of the artery by the small pressure area of the trapezoid protuberance section 102, the shoe member 107 with a suitable height can be used to increase the length of the raised protuberance section 102 of the artificial hand component 101. Or, in those patients, the artificial hand component 101 having a balloon member 108 can be used to add the needed height of the trapezoid protuberance section 102 by injecting air. Then, the metal weight component 106 is positioned on the artificial hand component 101 and after installing the treatment system, the bleeding of the zone of the perforation 602 and distal pulse pressure are controlled. Now, based on the doctor's decision, the transparent pressure dressing device 100 is placed on the hemostasis area for the needed amount of time. After finishing the task, the artificial hand component 101 is destroyed, but the metal weight component 106 is re-usable again after being cleaned and disinfected.

In real application, this transparent pressure dressing device 100 is used to stop bleeding in the zone of femoral artery perforation 602 in groin area after angiography and angioplasty. By compression of tissues above the vessel wall, it blocks the zone of femoral artery perforation 602, and as a result causes hemostasis. Furthermore, it may be used as a pressure dressing in some areas of the body where creating a suitable pressure is required to stop the bleeding such as arterial pseudoaneurysm, blocking the arteriovenous fistula, controlling the bleeding caused by needle biopsy, and in injured or operated zones.

Regarding the designing of the transparent pressure dressing device 100 the angles, the shape of the protuberance section 102 like a trapezoid, the size of the artificial hand component 101, lateral depressions as well as the location of the trapezoid-shaped protuberance section 102, the size of the surface of the protuberance section 102 and acute angle to the surface of the artificial hand component 101, etc., have been designed with the use of the anatomy of hemostasis area. The designing is performed in a way that the trapezoid surface of the artificial hand component 101 has the least involvement with the muscles, bones and ligaments of the groin area of the leg and covers, without any problem, the possible areas of several perforations 602 on the artery during the venipuncture as well as the angle of needle insertion and angiography sheet into the femoral artery with respect to the thickness of underlying tissue to the zone of the perforation 602 in obese or lean patients which may have to be, for example, 20 mm distance with the zone of skin perforation 602, and, therefore the maximum concentration is applied only on the femoral artery.

In contrast to the conventionally used devices, the main use of the transparent pressure dressing device 100 is that it carries out hemostasis completely, from the beginning of the arterial or venous sheath removal to the end of the process. But in other methods, first the initial hemostasis and then homeostasis maintenance, such as, using the sandbag, are performed. The transparent pressure dressing device 100 can be installed simply and very fast, for example, in less than 30 seconds. The transparent pressure dressing device 100 requires only a short time for creating full hemostasis, for example, about 3 hours, with respect to the patient's conditions such as blood pressure, coagulation disorders, obesity, etc. However, this is 6 hours in other methods because the pressure is fluctuating on the location. The maintenance of sterility of the transparent pressure dressing device 100, owing to the transparent disposable artificial hand component 101 and the capability of full cleaning of the metal weight component 106, is relatively very difficult in other methods, such as, sandbag.

Another aspect of the present disclosure is directed to a method of enabling hemostasis of blood in a perforation of a blood vessel. The method comprises: (a) providing a transparent pressure dressing device comprising (i) a rectangular plate shaped artificial hand component, wherein the artificial hand component comprises a protuberance section positioned proximal to a distal edge of the artificial hand component and (ii) one or more adhesive fins extending from an upper surface of the artificial hand component. The method further comprises marking the perforation of the blood vessel using a marker; aligning the protuberance section of the artificial hand component against the marked perforation on the blood vessel; and removing a cover of adhesive fins positioned on the upper surface of the artificial hand component. The method further comprises controlling the bleeding at the perforation by gradually applying pressure using the hand of trained personnel on the artificial hand component, wherein the protuberance section is pressed against the perforation of the blood vessel; and positioning one or more metal weight components above the artificial hand component. The method further comprises attaching the adhesive fins proximal to the perforation of the blood vessel; and retaining the transparent pressure dressing device over the perforation of the blood vessel for a predefined time until the hemostasis of blood is observed in the perforation of the blood vessel.

A first set of the adhesive fins may be attached to a leg of the patient, wherein one of the adhesive fins is attached on the abdomen toward an upper edge of a pelvis bone of a front leg, and the other adhesive fin on a side of the patient and upper edge of the pelvis bone of the leg. A second set of the adhesive fins may be removed and attached to the skin of the lower section of the patient's groin, on both internal and external sides of the patient's groin. In one example, a shoe member with a suitable height may be positioned over the protuberance section to increase the height of the raised protuberance section of the artificial hand component, wherein the shoe member enables to contact a blood vessel which is deeply positioned under the skin of the patient. The method may further comprise removably attaching a balloon member above the artificial hand component, wherein a vented pipe is attached to the balloon member to define a fluid communication with the balloon member. In one example, a fluid is pumped into through the vented pipe to expand the balloon member to increase pressing pressure at the perforation on the blood vessel with the artificial hand component.

One of the important aspects of this transparent pressure dressing device 100 is the direct visibility of the zone of the perforation 602 and the surrounding area constantly, due to the special design and the transparency of the artificial hand component 101. This enables for a user to view the possible occurrence of any bleeding and hematoma. But in other methods, coverage such as dressing, sandbag and the cover which is placed over the perforation 602 zone prevent the visibility of the area, and in the case of occurrence of any problem, and it will be visible only with bleeding and massive hematoma combined with the delay in understanding the condition, which is undesirable. The transparent pressure dressing device 100 creates pressure on a small area of the body with low weight force which prevents the patient from feeling the annoying pressure. In other methods, the dimensions of the devices are much bigger such as sandbag and C-shaped metal device.

The amount of added weights required is less in the case of the transparent pressure dressing device 100 compared to conventional devices, for example, about 0.5-1.5 kilogram (kg), for the initial hemostasis and homeostasis maintenance. But in other conventional devices, for example, 3-5 kg is required, and there will be the possibility of reduction or loss of blood flow which can cause pain in lower back and groin area in patients. There is no possibility of moving weights because the weights are fixed into the artificial hand component 101 with the magnetic force and the holding edge in the arcs. The transparent pressure dressing device 100 does not move by slight or even moderate movements of the patient, and remains constant on the installed place so the possibility of transferring the patient from stretcher to bed is easy. But in other methods, there is the possibility of the sandbag falling down or the C-shaped device being displaced.

In an embodiment, the transparent pressure dressing device 100 is a healthcare system which could be completely cleaned and sterilized. The artificial hand 101 of the pressure dressing device 100 is transparent and provided with precise and special design to concentrate and position pressure on a particular/required surface. Due to the transparency of the artificial hand 101, the position of the puncture could be visible by a user, where it helps in positioning and fixing the artificial hand 101 to the given zone by the adhesive fins 103. The area of the arterial sheath's removal could be visible via transparent device 100 so that in the case of bleeding and hematoma, the suitable actions could be taken immediately. To apply/create the required pressure on the artificial hand 101 of the pressure dressing device 100, the magnetic weight pieces and/or metal weight component with high density or with different weight could be incorporated. Henceforth, the said components could be attached together by means of magnetic force. In one embodiment, the present invention facilitates the compression of the underlying tissues of the body to block the zone of puncture by the pressure or force created/applied by the weights. In one embodiment, the pressure on the underlying tissues of the body could be adjusted by increasing and decreasing the number of metal weight components with similar or different weight. Furthermore, even in a small area of the body surface or a pressure zone, the artificial hand 101 is configured to compress the underlying tissues of the body, and concentrates the pressure on the pierced wall of the artery.

In one embodiment, the artificial hand 101 with curve like depressions 104 on its both sides so that the user could handle the device 100 from the curve like depressions 104 easily and have a better control on the device 100. The metal weight components 106 are attached to the curve like depressions 104 of the protuberance section 102 with the height ranges from 3 mm to 5 mm, which help the operator in handling the component 106, and preventing the slippage of the metal weight component 106 to the sides. By controlling bleeding and blocking the femoral artery perforation by compression of the underlying tissues with fixed pressure, leading to clot formation for improving the health condition of the user. In the artificial hand 101, the trapezoid shaped protuberance section 102 has been considered as the mean for application of pressure. After attaching the above adhesive fins, according to the designed shape of the artificial hand 101, the protuberance section 102 moves forward like a lever by lowering the end of the artificial hand component 101, and cause pressure on the femoral artery, where the said femoral artery is placed between the front of the protuberance section 102 and pelvic bone, and is placed on the opening of the arterial wall thereby increases the compression on the body surface or area. The height of the artificial hand 101 ranges from 20 to 80 mm, is fixed to the area/surface on four sides using four adhesive fins 103 in an approximately cross shape and creates concentrated pressure on the tissue of the small contact body surface. This prevents any movement or relocation of the device 100, where the pressure/force is applied.

The tensile force produced by four adhesive fins 103 on the artificial hand 101, and the force/pressure created by the weights are transferred to the trapezoid-like protuberance section 102 under the artificial hand 101, or the pressure zone, therein compressing the tissues of the body on the zone of artery perforation. By applying required amount of pressure on the given body surface using less weight on the user or patient body, the patients suffer less pain in the area being compressed or the pain in the waist or pelvis. Furthermore, with suitable concentration of pressure on the user's body surface/area, the trained health care workers need to create less pressure on the area being compressed by their body, and use weights for this aim. Thus, the workers are afflicted with fewer physical damages such as pain in the fingers, wrists, arms, shoulders and backs as well as fatigue.

In one embodiment, the small iron pieces or magnetic pieces used on the artificial hand 101 is matched with the installed iron pieces 105 or magnets on the metal weights components 106, such that the components 106 could be attached to prevent the relocation and falling on each other. In an embodiment, the metal weight component 106 is made of metals with high density, which have no effect on the magnetic force. In one embodiment, the metal weight component 106 uses iron piece on one side, and magnetic plates on the other side. In another embodiment, the metal weight component 106 uses magnetic plates on both sides. The pieces 105 could be with or without attachments to each other, to possess positive effects on the magnetic force. Therefore, there is no limitation on the number of the metal weight component 106 with attached weight pieces 105. To detach the components 106 or iron pieces 105, it is sufficed that the given weight revolves around its center and places in the perpendicular surface. The magnetic attraction force is reached to minimum by decreasing the contact surface of the magnetic components 106 of the above piece with the bottom iron piece 105. Then, by holding the bottom iron piece 105, it will be possible to remove the given component 106 without reducing the pressure or strain.

In one embodiment, the metal weight component 106 is coated with a suitable coating to provide infection control and safety conditions for patients and health care workers. For example, a scratch resistant color coating avoids formation of the scratches produced due to an impact or corrosion caused by disinfectants and detergents. The artificial hand 101 could be packed in a disposable package, and sterilized after production to provide infection control and safety conditions in hospitals. Henceforth, the present invention provides a useful role in establishing conditions to control nosocomial infection by eliminating sandbags in vascular homeostasis stages after coronary angiography and angioplasty. Further, there is a chance of large displacement from the zone of the vascular puncture while transferring patient from a bed to a stretcher, or from the stretcher to the bed. The device 100, involving attachment of the weights to the artificial hand with magnetic force, and the shape of the weights which have low height and high density, so the chance/possibility of displacement will be decreased dramatically.

In one embodiment, the dimension and shape of the metal weight component 106 could be adaptable to the requirement/need. The dimensions such as length, width and height of the artificial hand 101 could be smaller or bigger than the regular dimensions in the schemes in accordance with the physical conditions of the patient. The height of the protuberance section 102 in the artificial hand 101 ranges from 20 mm to 80 mm in accordance with the physical conditions of the patient. In some embodiments, the dimension of the artificial hand 101 could be adjustable based on lean or obese patients, which reduces the diversity of models of artificial hand 101. In one embodiment, the artificial hand 101 could be used in the areas wherein enough pressure is required by itself, for example, in case of control bleeding caused due to introduction of biopsy needle through the skin.

In one embodiment, the embossed protuberance of the artificial hand 101 could be placed and fixed as a pressure dressing in the biopsy area in different and needed forms such as circle, square, rectangle, oval, etc. in the middle or sides of the lower surface of the transparent artificial hand 101 with adhesive fins 103, and controls the bleeding by creating pressure on the underlying tissues based on the discretion of the doctor. In some embodiments, the artificial hand 101 along with shoe member 107 or balloon member 108 could be used to control bleeding in different forms and sizes based on the discretion of the doctor, without using the metal weight component 106 or the iron or metal pieces 105. The device 100 is used as a replacement for voluminous sterile gauze for pressure dressing. In one embodiment, the artificial hand 101 implemented with the balloon member 108, increases the efficiency of the device 100, and increase pressure transference by enhancing the height and using tensile force of the adhesive fins 103. The device 100 is adjustable to the contact surface of the component and the patient's skin with the balloon, and establishes the transference of the force. In another embodiment, the volume of the balloon member 108 could be increased by injecting air via vented pipe 109, thereby increasing the height of the trapezoid protuberance section 102 to increase the pressure, in cases such as, when there is a lack of sufficient length of the trapezoid protuberance section 102 in the artificial hand 101, and when there is an occurrence of blood leakage in the zone of the puncture.

The transparent pressure dressing device 100 reduces the cost of health care, because the trained personnel must carry out a patient's hemostasis in about 20 minutes. Some personnel need to have a well-trained staff at the same time, but with the help of transparent pressure dressing device 100, the hemostasis of several patients and other treatments such as serum or drug injection, connection of oxygen to the patient will be possible simultaneously with less number of trained health care workers. On the other hand, the metal weight component 106 is permanent. That is, the weights only need to be purchased once and can be used for an unlimited period of time. Each time, after using, it can be easily cleaned and disinfected. In addition, there is no need for more of gauze on the given area for creating a mass and increasing pressure in homeostasis site; therefore, it can be effective in reducing health care costs. The transparent pressure dressing device 100 be easily used on lean or obese patients.

With the use of the transparent pressure dressing device 100, the time and energy required from the medical staff will be saved dramatically, since the need to compress the zone of the perforation 602 by the hand of medical personnel will be reduced. The artificial hand and the weights are used for homeostasis based on the need to control bleeding and foot pulse of the patient. The medical personnel have controlling role rather than physical. The use of this the transparent pressure dressing device 100 is simple and easy which brings comfort to both patients and medical personnel.

The foregoing examples have been provided merely for the purpose of explanation and are in no way to be construed as limiting of the present concept disclosed herein. While the concept has been described with reference to various embodiments, it is understood that the words, which have been used herein, are words of description and illustration, rather than words of limitation. Further, although the concept has been described herein with reference to particular means, materials, and embodiments, the concept is not intended to be limited to the particulars disclosed herein; rather, the concept extends to all functionally equivalent structures, methods and uses, such as are within the scope of the appended claims. Those skilled in the art, having the benefit of the teachings of this specification, may affect numerous modifications thereto and changes may be made without departing from the scope and spirit of the concept in its aspects.

What is claimed is:

1. A transparent pressure dressing device configured to enable hemostasis of blood in a perforation of a blood vessel, the transparent pressure dressing device comprising;
   a rectangular plate shaped artificial hand component, wherein the artificial hand component comprises a protuberance section positioned proximal to a distal edge of the artificial hand component; and
   one or more adhesive fins extending from an upper surface of the artificial hand component, wherein the protuberance section of the artificial hand component is configured to be gradually pressed against the perforation on the blood vessel to enable hemostasis of the blood, and the adhesive fins are configured to adhere to a body surface of a patient proximal to the perforation on the blood vessel; and
   further comprising one or more metal weight components positioned above and conforming to the upper surface of the artificial hand component, wherein each metal weight component is configured to add weight to the artificial hand component to increase the pressure applied to enable hemostasis of the blood at the perforation of the blood vessel; and
   further comprising a plurality of magnetic pieces positioned on an upper surface of each metal weight component, wherein the magnetic pieces allow attachment of the one or more metal weight components above the artificial hand component to generate required compression on body's tissues proximal to the perforation of the blood vessel.

2. The transparent pressure dressing device of claim 1, wherein any one of the surfaces of the magnetic pieces is one of electroplated and stretched with a cover made of polymer material to preserve an integral surface of attachment.

3. The transparent pressure dressing device of claim 1, further comprising a transparent adhesive plastic layer positioned on the upper the surface of the artificial hand component, wherein the adhesive plastic layer enables alignment of the magnetic pieces and the adhesive fins.

4. The transparent pressure dressing device of claim 1, wherein the protuberance section is configured to transfer pressure to underlying tissues proximal to the perforation of the blood vessel to block the blood flow at the perforation, thereby stopping the bleeding through hemostasis.

5. The transparent pressure dressing device of claim 1, further comprising a trapezoid shaped shoe member, wherein the shoe member is configured to conform to an upper surface of the protuberance section, wherein the shoe member is configured to provide added height to the protuberance section to enable a deeper application of pressure at the perforation on the blood vessel.

6. The transparent pressure dressing device of claim 1, further comprising a balloon member removably attached above the artificial hand component, wherein a vented pipe is attached to the balloon member to define a fluid communication with the balloon member, wherein a fluid is pumped into through the vented pipe to expand the balloon member to increase pressing pressure at the perforation on the blood vessel via the artificial hand component.

7. The transparent pressure dressing device of claim 1, wherein the artificial hand component is disposable after the hemostasis of the blood is completed.

8. The transparent pressure dressing device of claim 1, wherein the metal weight components are re-usable after the hemostasis of the blood is completed, wherein the metal weight components are re-usable via cleaning and disinfection.

9. The transparent pressure dressing device of claim 1, wherein another set of adhesive fins are attached to bottom corners of the artificial hand component to adhere to the body surface of the patient proximal to the perforation on the blood vessel.

* * * * *